United States Patent [19]

Saupe et al.

[11] Patent Number: 5,258,356

[45] Date of Patent: * Nov. 2, 1993

[54] SUBSTITUTED 1,8-NAPHTHYRIDINES, THEIR PREPARATION AND THEIR USE AS ANTIDOTES

[75] Inventors: Thomas Saupe, Sandhausen; Peter Schaefer, Bad Durkheim; Norbert Meyer, Ladenburg; Bruno Wuerzer, Otterstadt; Karl-Otto Westphalen, Speyer, all of Fed. Rep. of Germany

[73] Assignee: BASF Aktiengesellschaft, Ludwigshafen, Fed. Rep. of Germany

[ * ] Notice: The portion of the term of this patent subsequent to Oct. 22, 2008 has been disclaimed.

[21] Appl. No.: 13,202

[22] Filed: Feb. 1, 1993

Related U.S. Application Data

[60] Continuation of Ser. No. 639,372, Jan. 10, 1991, abandoned, which is a division of Ser. No. 489,903, Mar. 7, 1990, abandoned.

[30] Foreign Application Priority Data

Mar. 11, 1989 [DE] Fed. Rep. of Germany ....... 3907937

[51] Int. Cl.$^5$ .............................................. A01N 25/32
[52] U.S. Cl. .................... 504/105; 504/289; 504/344
[58] Field of Search ........................ 504/105, 289, 344

[56] References Cited

U.S. PATENT DOCUMENTS

| 2,517,929 | 8/1950 | Richter ................................. 546/122 |
| 3,564,768 | 2/1971 | Hoffman .................................... 71/3 |
| 4,133,885 | 1/1979 | Bolhofer et al. ..................... 424/256 |
| 4,249,937 | 2/1981 | Iwataki et al. ........................... 71/98 |
| 4,753,933 | 6/1988 | Cotrel et al. ........................ 546/122 |
| 4,822,884 | 4/1989 | Hubele ..................................... 71/94 |
| 4,881,969 | 11/1989 | Saupe et al. ............................. 71/94 |
| 5,059,240 | 10/1991 | Hagen et al. ............................ 71/94 |

FOREIGN PATENT DOCUMENTS 1088659 10/1980 Canada .
0329012 8/1989 European Pat. Off. .

OTHER PUBLICATIONS

Henry et al., *J. Het. Chem.* 14, 1109–1114 (1977).
Carboni et al., *Ann di Chim.* 54, 883–890 (1964).
Lappin et al., *J. Org. Chem.* 15, 377–380 (1950).
Mangini et al., *Gazz. Chim. it al.*-73, 330–334 (1943).

(List continued on next page.)

*Primary Examiner*—Allen J. Robinson
*Assistant Examiner*—John D. Pak
*Attorney, Agent, or Firm*—Keil & Weinkauf

[57] ABSTRACT

A combination of a variety of herbicides with safening agents which are substituted 1,8-naphthyridines of the formula $$\underset{R^7}{\overset{R^6}{\diagdown}}\underset{N}{\overset{R^5}{\diagdown}}\underset{N}{\diagdown}R^1 \qquad I$$

where
$R^1$ is mercapto, hydroxyl, halogen, benzylthio, amino or $NR^2R^3$, where
$R^2$ is a group $$-\overset{\overset{O}{\|}}{C}-A,$$

where A is $C_1$–$C_8$-alkyl,
$R^3$ is hydrogen, $XR^4$, where X is oxygen or sulfur and $R^4$ is $C_1$–$C_{12}$-alkyl,
$R^5$ and $R^7$ are each hydrogen, $C_1$–$C_{12}$-alkyl, hydroxyl, halogen, mercapto, $C_1$–$C_4$-alkoxy, $C_1$–$C_4$-alkylthio, dialkylamino where each alkyl is of 1 to 6 carbon atoms, phenoxy or phenylthio, halo-($C_1$–$C_3$)-alkyl, $C_1$–$C_4$-alkoxy-($C_1$–$C_3$)-alkyl, and
$R^6$ is hydrogen, $C_1$–$C_{12}$-alkyl, carboxyl or $C_1$–$C_4$-alkoxycarbonyl or the plant-tolerated salts thereof.

9 Claims, No Drawings

OTHER PUBLICATIONS

Petrow et al., *J. Chem. Soc. London*, 1407–1410 (1947).
Seide, *Chem. Berichte*, LIX, 159–164 (1926).
Bernstein et al., *J. Am. Chem. Soc*, 69, 1147–1150 (1947).
Mangini et al., *Gazz. Chim. it al.* 73, 323–329 (1947).
Ochiai et al., *Chem. Berichte* 74, 1115–1127 (1941).
Carboni et al., *Gazz chim. it al.*, 101, 129–138 (1971).
Carboni et al., *Gazz. chim. it al.*, 95, 1492–1501 (1965).
Brown, *J. Org. Chem.* 30, 1607–1610 (1965).
Eichler et al., *J. Het. Chem.* 13, 41–42 (1976).
Bolhofer et al., *J. Med. Chem.* 22(3), 301–306 (1979).
Comprehensive Heterocyclic Chem. (Katritsky and Rees) vol. 2, Naphthyridines, Pyridoquinolines, Anthyridines and Similar Compounds, P. A. Lowe, University of Salford pp. 581–627 (1984).
Tetrahedron Report No. 92, Heteroannelations with o-Aminoaldehydes Tetrachron vol. 36 pp. 2359–2407, Caluwe (1980).
*J. Chem. Society,* Hawes et al., "1,8-Naphthyridines", 1967, pp. 1564–1568.

SUBSTITUTED 1,8-NAPHTHYRIDINES, THEIR PREPARATION AND THEIR USE AS ANTIDOTES

This application is a continuation of application Ser. No. 07/639,372, filed on Jan. 10, 1991, now abandoned, which is a divisional of application Ser. No. 07/489,903, filed on Mar. 7, 1990, now abandoned.

The present invention relates to substituted 1,8-naphthyridines of the general formula I

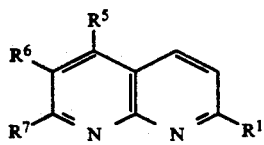

where $R^1$ is mercapto, benzylthio, sulfonyl, amino or $NR^2R^3$, $R^2$ is $C_1$–$C_{12}$-alkyl, $C_3$–$C_6$-alkenyl, $C_3$–$C_8$-cycloalkyl, phenyl, phenyl-$C_1$–$C_3$-alkyl or phenyl or phenyl-$C_1$–$C_3$-alkyl which is monosubstituted to trisubstituted by halogen, $C_1$–$C_4$-alkyl, $C_1$–$C_4$-alkoxy, amino, or mono- or dialkylamino where each alkyl radical is of 1 to 6 carbon atoms, or a group

where A is $C_1$–$C_8$-alkyl or is phenyl which is unsubstituted or monosubstituted to trisubstituted by halogen, $C_1$–$C_4$-alkyl, $C_1$–$C_4$-alkoxy, amino or mono- or dialkylamino where each alkyl radical is of 1 to 6 carbon atoms, or is amino, alkylamino or dialkylamino where each alkyl radical is of 1 to 6 carbon atoms, phenylamino, morpholino or piperidyl, and $R^3$ is hydrogen, $C_1$–$C_{12}$-alkyl or $C_3$–$C_8$-cycloalkyl, or $R^2$ and $R^3$ are bonded to one another to form a saturated or unsaturated 5-membered or 6-membered heterocyclic structure which, in addition to the nitrogen atom to which they are bonded, may contain a further heteroatom, such as oxygen or nitrogen hydroxyl, mercapto, halogen or $XR^4$ where X is oxygen or sulfur and $R^4$ is $C_1$–$C_{12}$-alkyl, $C_1$–$C_4$-alkoxycarbonyl-$C_1$–$C_4$-alkyl, $C_5$–$C_8$-cycloalkyl, phenyl or phenyl-$C_1$–$C_3$-alkyl, where the aromatic rings may carry from one to three of the following radicals: halogen, $C_1$–$C_4$-alkyl, $C_1$–$C_4$-alkoxy, amino or mono- or dialkylamino, where each alkyl radical is of 1 to 6 carbon atoms, $R^5$ and $R^7$ are each hydrogen, $C_1$–$C_{12}$-alkyl, or $C_3$–$C_8$-cycloalkyl, phenyl or phenyl-$C_1$–$C_3$-alkyl, where the phenyl nucleus in each case may in turn carry from one to three of the following groups: halogen, $C_1$–$C_4$-alkyl, $C_1$–$C_4$-alkoxy, $C_1$–$C_4$-haloalkyl, amino or mono- or dialkylamino where each alkyl radical is of 1 to 4 carbon atoms; hydroxyl, halogen, mercapto, $C_1$–$C_4$-alkoxy, $C_1$–$C_4$-alkylthio, amino, mono- or dialkylamino, where each alkyl radical is of 1 to 6 carbon atoms, phenoxy or phenylthio, where the phenyl nucleus in each case may in turn carry from one to three of the following groups: halogen, $C_1$–$C_4$-alkyl, $C_1$–$C_4$-alkoxy, $C_1$–$C_4$-haloalkyl, amino or mono-or dialkylamino where each alkyl radical is of 1 to 4 carbon atoms; halo-$C_1$–$C_3$-alkyl, $C_1$–$C_4$-alkoxy-$C_1$–$C_3$-alkyl, $C_1$–$C_4$-alkylthio-$C_1$–$C_3$-alkyl, amino-$C_1$–$C_3$-alkyl, $C_1$–$C_4$-acyloxy, hydrazino which may carry from one to three $C_1$–$C_4$-alkyl radicals and/or a $C_1$–$C_4$-acyl radical; cyano or thiocyanato, and $R^6$ is hydrogen, $C_1$–$C_{12}$-alkyl, $C_3$–$C_8$-cycloalkyl, phenyl or phenyl-$C_1$–$C_3$-alkyl, where the phenyl nucleus in each case may in turn carry from one to three of the following groups: halogen, $C_1$–$C_4$-alkyl, $C_1$–$C_4$-alkoxy, $C_1$–$C_4$-haloalkyl, amino or mono- or dialkylamino, where each alkyl radical is of 1 to 4 carbon atoms; halogen, halo-$C_1$–$C_3$-alkyl, $C_1$–$C_4$-alkoxy-$C_1$–$C_3$-alkyl, $C_1$–$C_4$-alkylthio-$C_1$–$C_3$-alkyl, amino-$C_1$–$C_3$-alkyl, carboxyl or $C_1$–$C_4$-alkoxycarbonyl, and their plant-tolerated salts.

The present invention furthermore relates to a process for the preparation of the compounds I and herbicides which contain the 2-(4-hetaryloxy)- or 2-(4-aryloxy)-phenoxyacetic acid derivatives or propionic acid derivatives and/or cyclohexenone derivatives as herbicidal active ingredients and substituted 1,8-naphthyridines as antidotes, and methods for selectively controlling undesirable plant growth with these herbicides.

An overview of the preparation of various 1,8-naphthyridine derivatives is given by P. A. Lowe in Comprehensive Heterocyclic Chemistry (editors: A. R. Katritzky and C. W. Rees), Vol. 2, 1st edition (1984), Chapter 2.11. The synthesis of 1,8-naphthyridine derivatives is also described by P. Caluwe in Tetrahedron 36 (1980), 2359–2407, in particular 2391–2394.

The crop protection activity of this class of compound is not evident from the prior art.

Herbicidal active ingredients from the group consisting of the 2-(4-hetaryloxy)- or 2-(4-aryloxy)-phenoxyacetic acid derivatives of the formula IV

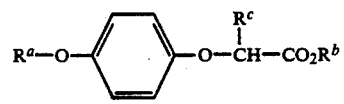

where $R^a$ is a phenyl ring, a pyridyl ring, a benzoxazyl radical, a benzthiazyl radical or a benzopyrazinyl radical, and these aromatic ring systems may carry up to two of the following radicals: halogen, nitro, $C_1$–$C_4$-alkyl, $C_1$–$C_4$-haloalkyl and/or $C_1$–$C_4$-haloalkoxy, $R^b$ is hydrogen, $C_1$–$C_4$-alkyl or one equivalent of a plant-tolerated cation and $R^c$ is hydrogen or methyl, are disclosed in the literature, for example in DE-A-22 23 894, DE-A-24 33 067, DE-A-25 76 251, DE-A-30 04 770, BE-A-868 875 and BE-A-858 618.

They are used for controlling undesirable plants from the Gramineae family. However, the tolerance of these substances by crops varies between commercially acceptable and non-tolerated, depending on the substituents and application rate.

The same situation is encountered with cyclohexenone derivatives of the formula V

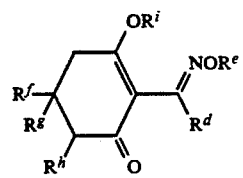

where
$R^d$ is $C_1$–$C_4$-alkyl;
$R^e$ is $C_1$–$C_4$-alkyl, $C_3$- or $C_4$-alkenyl, $C_3$- or $C_4$-alkynyl, $C_3$- or $C_4$-haloalkylene or thenyl which may be substituted by a halogen atom;

$R^f$ is $C_1$–$C_4$-alkyl which may be monosubstituted or disubstituted by $C_1$–$C_4$-alkylthio or $C_1$–$C_4$-alkoxy;

a 5-membered or 6-membered saturated or monounsaturated ring system which, in addition to carbon members, may contain an oxygen or sulfur atom or a sulfoxyl or sulfonyl group, and this ring may carry up to three of the following radicals: hydroxyl, halogen, $C_1$–$C_4$-alkyl, $C_1$–$C_4$-haloalkyl, $C_1$–$C_4$-alkoxy and/or $C_1$–$C_4$-alkylthio;

a 10-membered saturated or monounsaturated heterocyclic structure which contains two oxygen atoms or sulfur atoms and may be substituted by up to three $C_1$–$C_4$-alkyl groups and/or methoxy groups;

a phenyl, pyridyl, thiazolyl, pyrazolyl, pyrrolyl or isoxazolyl radical which may carry up to three of the following groups: $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-dialkoxy-$C_1$–$C_3$-alkyl, formyl, halogen and/or benzoylamino, $R^g$ is hydrogen or hydroxyl or, when $R^f$ is $C_1$–$C_6$-alkyl, is $C_1$–$C_6$-alkyl;

$R^h$ is hydrogen, cyano, halogen, $C_1$–$C_4$-alkoxycarbonyl or a $C_1$–$C_4$-alkylketoxime group and $R^i$ is hydrogen or one equivalent of an environmentally compatible cation.

They are likewise described in the literature (e.g. EP-A 228 598, EP-A 230 235, EP-A 238 021, US-A 4 432 786, DE-A 24 39 104) as herbicides and are predominantly used for controlling undesirable grasses in dicotyledon crops and in grasses which do not belong to the Gramineae family. Depending on the structure of the substituents and the application rate, compounds of this group can also be used for selectively controlling undesirable grasses in gramineous crops, such as wheat and rice.

It is an object of the present invention to provide compounds which at least reduce the disadvantages encountered in using the abovementioned herbicides of the formulae IV and V to such an extent that the harvest yield of the crops is not significantly reduced, if at all.

We have found that this object is achieved by the substituted 1,8-naphthyridines I defined at the outset. We have also found processes for the preparation of these compounds I and for the joint use of these compounds with the herbicides IV and V for influencing undesirable plant growth. The present invention furthermore relates to agents which contain the compounds I, and it is unimportant whether the herbicidal active ingredient and the antidote compound are formulated and applied together or separately or, in the case of separate application, in which order the herbicidal active ingredient and the antidote are applied.

The novel compounds I are obtainable by reacting 2,6-diaminopyridine II with a β-dicarbonyl compound III.

The substitution pattern can be varied within a wide range by appropriate choice of the β-dicarbonyl compound III; in addition to 1,3-diketones, malonaldehydes or their acetals and β-ketoaldehydes or their acetals, it is also possible to use malonic esters, β-keto esters and β-formyl esters or their acetals for the cyclocondensation to give I.

The preparation of I is illustrated by the following equations:

where, for example, $R^5$ and $R^7$ are each H, alkyl, cycloalkyl, phenyl, phenylalkyl, haloalkyl or alkoxyalkyl and $R^6$ is H, alkyl, cycloalkyl, phenyl, phenylalkyl, halogen, haloalkyl or alkoxyalkyl The structural isomers Ia and Ib are formed as a mixture but can be obtained individually by conventional separation methods, for example by recrystallization or chromatography.

2- or 4-hydroxy-1,8-naphthyridines Ia and Ib and 2,4-dihydroxy-1,8-naphthyridines Ic react with a halogenating agent, such as phosphorous oxychloride or -bromide to give 2- or 4-halonaphthyridines or 2,4-dihalonaphthyridines, respectively. By reactions to exchange the halogen for N, S or O nucleophiles and C nucleophiles, such as cyanide, the substitution pattern of I can be varied within a wide range.

Furthermore, the primary amino function of the substituted 1,8-naphthyridines I can be derivatized in a conventional manner, for example alkylated or acylated. It is also possible to convert the primary amino group of I into a hydroxyl group by diazotization in acidic aqueous solution and boiling of the resulting diazonium salt.

The substituted 1,8-naphthyridines I where $R^1$ is OH, which are prepared in this manner, react with halogenating agents, such as phosphorus oxychloride or -bromide in a manner similar to that described above to give the corresponding 1,8-naphthyridines I where $R^1$ is halogen.

The halogen introduced in this manner in place of the primary amino function of I can undergo the abovementioned nucleophilic exchange reactions so that further variations of the substitution pattern of I are possible.

Usually, the starting materials II and III are used in a stoichiometric ratio. However, an excess of one or other may be quite advantageous in specific cases.

The reaction can be carried out continuously or batchwise under atmospheric, superatmospheric or reduced pressure using the conventional methods. The reaction temperature is in general from 20° to 400° C., in particular from 50° to 300° C., advantageously in the boiling range to the solvent.

Advantageously used solvents and condensing agents are acids, such as sulfuric acid, phosphoric acid, acetic acid and mixtures thereof, and relatively high-boiling ethers, such as diphenyl ether, dioxane or tetrahydrofuran. In certain cases, it may also be advantageous to heat the two starting compounds I and II in the absence of a solvent.

In addition to the abovementioned solvents, however, other suitable ones are aliphatic and aromatic hydrocarbons and chlorohydrocarbons.

In view of the intended use of the compounds I as crop protection agents, suitable substituents are the following radicals:

$R^1$ is mercapto, benzylthio, hydroxyl, $C_1$–$C_4$-alkoxy, sulfonyl ($SO_3H$), amino or $NR^2R^3$, where $R^2$ is $C_1$–$C_{12}$-alkyl, $C_3$–$C_6$-alkenyl, $C_3$–$C_8$-cycloalkyl, phenyl, phenyl-$C_1$–$C_3$-alkyl or phenyl or phenyl-$C_1$–$C_3$-alkyl which is substituted by halogen, $C_1$–$C_4$-alkyl, $C_1$–$C_4$-alkoxy, amino or mono- or dialkylamino where each alkyl radical is of 1 to 6 carbon atoms, or a group

where A is $C_1$–$C_8$-alkyl or is phenyl which is unsubstituted or monosubstituted to trisubstituted by halogen, $C_1$–$C_4$-alkyl, $C_1$–$C_4$-alkoxy, amino or mono- or dialkylamino where each alkyl radical is of 1 to 6 carbon atoms, or is amino, alkyl- or dialkylamino where each alkyl radical is of 1 to 6 carbon atoms, phenylamino, morpholino or piperidyl, and $R^3$ is hydrogen, $C_1$–$C_{12}$-alkyl or $C_3$–$C_8$-cycloalkyl, or $R^2$ and $R^3$ are bonded to one another to form a saturated or unsaturated 5-membered or 6-membered heterocyclic structure which may contain a further heteroatom, such as oxygen or nitrogen;

hydroxyl, mercapto, halogen, in particular fluorine, chlorine or bromine, or $XR^4$ where X is oxygen or sulfur and $R^4$ is $C_1$–$C_{12}$-alkyl, $C_1$–$C_4$-alkoxycarbonyl-$C_1$–$C_4$-alkyl, $C_5$–$C_8$-cycloalkyl, phenyl which is unsubstituted or substituted by halogen, $C_1$–$C_4$-alkyl, $C_1$–$C_4$-alkoxy, amino or mono- or dialkylamino where each alkyl radical is of 1 to 6 carbon atoms, or unsubstituted or substituted phenyl-$C_1$–$C_3$-alkyl, $R^5$ and $R^7$ are each hydrogen, $C_1$–$C_{12}$-alkyl, in particular $C_1$–$C_8$-alkyl, particularly preferably $C_1$–$C_4$-alkyl as stated for $R^2$, $C_3$–$C_8$-cycloalkyl, in particular cyclopropyl, cyclopentyl or cyclohexyl, phenyl or phenyl-$C_1$–$C_3$-alkyl, where the phenyl nucleus in each case is unsubstituted or substituted by $C_1$–$C_4$-alkyl, halogen, such as fluorine, chlorine or bromine, $C_1$–$C_4$-alkoxy, such as methoxy, ethoxy, propoxy, isopropoxy, butoxy or tert-butoxy, $C_1$–$C_4$-haloalkyl, e.g., $CF_3$, amino or mono- or dialkylamino where each alkyl radical is of 1 to 4 carbon atoms, particularly suitable phenylalkyl radicals being unsubstituted or substituted benzyl or phenylethyl, hydroxyl, mercapto, halogen, such as chlorine or bromine, $C_1$–$C_4$-alkoxy or alkylthio, such as methoxy, ethoxy, propoxy, isopropoxy, butoxy, tert-butoxy or the corresponding alkylthio radicals, amino, mono- or dialkylamino where each alkyl radical is of 1 to 6 carbon atoms, for example as stated for $R^2$, phenoxy or phenylthio, where the phenyl nucleus in each case may carry the substituents stated for phenyl or phenyl-$C_1$–$C_3$-alkyl, halo-$C_1$–$C_3$-alkyl, e.g. trifluoromethyl, trichloromethyl or 1,2-difluoroethyl, $C_1$–$C_4$-alkoxy- or -alkylthio-$C_1$–$C_3$-alkyl, e.g. methoxymethyl or methylmercaptomethyl, amino-$C_1$–$C_3$-alkyl, e.g. dimethylaminomethyl, $C_1$–$C_4$-acyloxy, hydrazino which is unsubstituted or substituted by one to three $C_1$–$C_4$-alkyl radicals, in particular by two geminal or vicinal $C_1$–$C_4$-alkyl radicals, e.g. methyl or ethyl, or is monoacylated, suitable acyl radicals being $C_1$–$C_4$-acyl, in particular acetyl, cyano or thiocyanato, and $R^6$ is hydrogen, $C_1$–$C_{12}$-alkyl, in particular $C_1$–$C_4$-alkyl as stated for $R^2$, $C_3$–$C_8$-cycloalkyl, in particular cyclopropyl, cyclopentyl, cyclohexyl, unsubstituted or substituted phenyl or phenyl-$C_1$–$C_3$-alkyl as stated for $R^5$ and $R^7$, halogen or halo-$C_1$–$C_3$-alkyl, in each case as stated for $R^5$ and $R^7$, $C_1$–$C_4$-alkoxy- or -alkylthio- or amino-$C_1$–$C_3$-alkyl, in each case as stated for $R^5$ and $R^7$, carboxyl and $C_1$–$C_4$-alkoxycarbonyl, e.g. methoxycarbonyl or ethoxycarbonyl.

Suitable salts of the compounds of the formula I are agriculturally suitable salts, for example alkali metal salts, in particular the potassium or sodium salt, alkaline earth metal salts, in particular the calcium, magnesium or barium salt, manganese salts, copper salts, zinc salts or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Specific examples herbicidal (hetaryloxy)- or aryloxyphenoxyacetic acid derivatives of the formula IV whose toleration by crops can be improved by substituted 1,8-naphthyridines of the formula I are listed in Table A below.

TABLE A

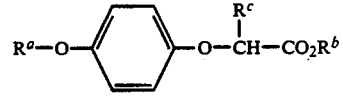

| No. | $R^a$ | $R^b$ | $R^c$ | Lit |
|---|---|---|---|---|
| IV.1 | (2,4-dichlorophenyl) | CH$_3$ | CH$_3$ | DE-A 22 23 894 |
| IV.2 | (trifluoromethyl-pyridyl) | n-C$_2$H$_9$ | CH$_3$ | BE-A 868-875 |
| IV.3 | (N-acetyl-chlorophenoxy) | C$_2$H$_5$ | CH$_3$ | BE-A 858 618 |

TABLE A-continued

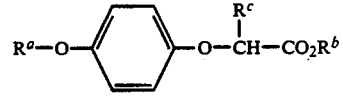

| No. | $R^a$ | $R^b$ | $R^c$ | Lit |
|---|---|---|---|---|
| IV.4 | (chloro-trifluoromethyl-pyridyl) | CH$_3$ | CH$_3$ | BE-A 868 875 |
| IV.5 | (chloroquinoxalinyl) | C$_2$H$_5$ | CH$_3$ | DE-A 30 04 770 |

Specific examples of cyclohexenones of the formula V whose tolerance by crop plants can be improved by substituted 1,8-naphthyridines of the formula I are given in Table B below.

TABLE B

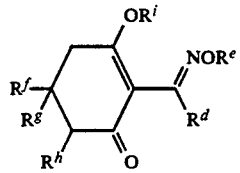

| No. | $R^d$ | $R^e$ | $R^f$ | $R^g$ | $R^h$ | $R^i$ | Literature |
|---|---|---|---|---|---|---|---|
| V.1 | C$_3$H$_7$ | CH$_2$CH=CH$_2$ | CH$_3$ | CH$_3$ | CO$_2$H$_3$ | Na | DE-A 2 439 104 |
| V.2 | C$_3$H$_7$ | CH$_2$CH$_3$ | CH$_2$CH(CH$_3$)SCH$_2$CH$_3$ | H | H | H | DE-A 2 822 304 |
| V.3 | C$_2$H$_5$ | CH$_2$CH=CHCl | CH$_2$CH(CH$_3$)SCH$_2$CH$_3$ | H | H | H | US-A 4 440 566 |
| V.4 | C$_3$H$_7$ | CH$_2$CH=CHCl | CH$_2$CH(CH$_3$)SCH$_2$CH$_3$ | H | H | H | US-A 4 440 566 |
| V.5 | C$_3$H$_7$ | C$_2$H$_5$ | (tetrahydrothiopyranyl) | H | H | H | EP-A 71 707 |
| V.6 | C$_2$H$_5$ | C$_2$H$_5$ | (tetrahydrothiopyranyl) | H | H | H | EP-A 71 707 |
| V.7 | CH$_3$ | CH$_2$CH=CHCH$_3$ | (tetrahydrothiopyranyl) | H | H | H | EP-A 71 707 |
| V.8 | C$_3$H$_7$ | C$_2$H$_5$ | (tetrahydropyranyl) | H | H | H | EP-A 71 707 |
| V.9 | C$_2$H$_5$ | CH$_2$CH=CHCl | (tetrahydropyranyl) | H | H | H | EP-A 142 741 |

TABLE B-continued $$\text{V}$$

Structure: cyclohexenone with $OR^i$, $=NOR^e$ on $R^d$-bearing substituent, $R^f$, $R^g$, $R^h$ substituents.

| No. | $R^d$ | $R^e$ | $R^f$ | $R^g$ | $R^h$ | $R^i$ | Literature |
|---|---|---|---|---|---|---|---|
| V.10 | $C_3H_7$ | $C_2H_5$ | 3-pyridyl | H | H | H | EP-A 66 195 |
| V.11 | $C_2H_5$ | $C_2H_5$ | 4-methylphenyl | H | H | H | DE-A 24 39 104 |
| V.12 | $C_2H_5$ | $CH_2CH=CHCH_3$ | 4-ethylphenyl | H | H | H | DE-A 38 08 072 |
| V.13 | $C_2H_5$ | $C_2H_5$ | 2,4,6-trimethylphenyl | H | H | H | EP-A 80 301 |
| V.14 | $C_3H_7$ | $CH_2CH=CHCl$ | 4-methylcyclohexyl | H | H | H | EP-A 88 299 |
| V.15 | $C_3H_7$ | $CH_2CH=CHCH_3$ | 4-methylcyclohexyl | H | H | H | EP-A 88 299 |
| V.16 | $C_2H_5$ | $CH_2CH=CHCH_3$ | 3-isopropyl-5-methylisoxazol-4-yl | H | H | H | EP-A 238 021 |
| V.17 | $C_3H_7$ | $CH_2CH=CHCH_3$ | 3-isopropyl-5-methylisoxazol-4-yl | H | H | H | EP-A 238 021 |
| V.18 | $C_2H_5$ | $CH_2CH=CHCl$ | 4-(propargyloxy)phenyl | H | H | H | EP-A 137 174 |
| V.19 | $C_3H_7$ | $C_2H_5$ | 4-(ethoxymethyl)phenyl | H | H | H | GB-A 2 137 200 |
| V.20 | $C_3H_7$ | $C_2H_5$ | 3,4-dibromotetrahydropyran-3-yl | H | H | H | EP-A 230 235 |

TABLE B-continued

V

[Structure: cyclohexenone with OR$^i$ at one position, C(=NOR$^e$)R$^d$ at adjacent position, R$^f$ and R$^g$ at another carbon, R$^h$ at another position]

| No. | R$^d$ | R$^e$ | F$^f$ | R$^g$ | R$^h$ | R$^i$ | Literature |
|---|---|---|---|---|---|---|---|
| V.21 | C$_3$H$_7$ | CH$_2$CH=CHCl | 3-bromo-4-bromo-tetrahydropyran | H | H | H | EP-A 230 235 |
| V.22 | C$_3$H$_7$ | CH$_2$CH=CHCl | 2,6,6-trimethylcyclohex-1-enyl | H | H | H | EP-A 46 860 |
| V.23 | C$_3$H$_7$ | C$_2$H$_5$ | cyclohexyl | H | H | H | JP-A 540 191 945 |
| V.24 | C$_3$H$_7$ | C$_2$H$_5$ | cyclohex-1-enyl | H | H | H | EP-A 46 860 |
| V.25 | CH$_3$ | CH$_2$CH=CHCl | 4-methylcyclohexyl | H | H | H | EP-A 88 299 |
| V.26 | C$_3$H$_7$ | C$_2$H$_5$ | 4-(trifluoromethyl)phenyl | H | H | H | EP-A 137 174 |
| V.27 | C$_2$H$_5$ | CH$_2$CH=CHCl | 2,6,6-trimethylcyclohex-1-enyl | H | H | H | EP-A 46 860 |
| V.28 | C$_3$H$_7$ | CH$_2$CH=CHCH$_3$ | 2-methyl-5-methylthiazol-4-yl | H | H | H | EP-A 125 094 |
| V.29 | C$_3$H$_7$ | CH$_2$CH=CHCl | 2-methyl-5-methylthiazol-4-yl | H | H | H | EP-A 125 094 |

TABLE B-continued

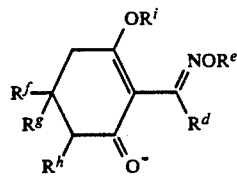

| No. | $R^d$ | $R^e$ | $R^f$ | $R^g$ | $R^h$ | $R^i$ | Literature |
|---|---|---|---|---|---|---|---|
| V.30 | $C_3H_7$ | $C_2H_5$ | 2,3,5-trimethylcyclohexyl | H | H | H | EP-A 88 299 |
| V.31 | $C_3H_7$ | $H_2CH=CH_2$ | 1-hydroxy-1-methyl-2-(ethylthio)-4-methylcyclohexyl | H | H | H | EP-A 228 598 |
| V.32 | $C_2H_5$ | $C_2H_5$ | 2,3-dihydroxy-5-methylcyclohexyl | H | H | H | EP-A 228 598 |
| V.33 | $C_3H_7$ | $C_2H_5$ | 1-methyl-3-methylpyrazol-5-yl | H | H | H | EP-A 66 195 |
| V.34 | $C_3H_7$ | $CH_2CH=CHCl$ | 1-methyl-3-methylpyrrol-5-yl | H | H | H | EP-A 66195 |
| V.35 | $C_3H_7$ | $CH_2CH=CH_2$ | 2-methyl-4-methylthiazol-5-yl | H | H | H | EP-A 125 094 |
| V.36 | $C_3H_7$ | $C_3H_7$ | $CH(SCH_2CH_3)_2$ | H | H | H | EP-A 230 260 |
| V.37 | $C_3H_7$ | $C_2H_5$ | 3-methyltetrahydrothiopyran-1-oxide | H | H | H | EP-A 115 808 |
| V.38 | $C_3H_7$ | $C_2H_5$ | 4-methyl-1,1-dioxotetrahydrothiopyran | H | H | H | EP-A 115 808 |
| V.39 | $C_3H_7$ | $C_2H_5$ | $CH_3$ | $CH_3$ | $C(CH_3)=NOCH_3$ | H | EP-A 172 551 |

TABLE B-continued

Structure V:

Cyclohexenone with substituents OR$^i$, NOR$^e$, R$^f$, R$^g$, R$^h$, R$^d$ and ketone

| No. | R$^d$ | R$^e$ | R$^f$ | R$^g$ | R$^h$ | R$^i$ | Literature |
|---|---|---|---|---|---|---|---|
| V.40 | C$_3$H$_7$ | CH$_2$CH=CH$_2$ | tetrahydrothiopyranyl-S,S-dioxide | OH | H | H | Proceedings Brit. Crop Protection Conference - Weeds 1985 Vol. 1 pp 93–98 |

The herbicidal active ingredients and antidotes may be applied together or separately to the leaves and shoots of the crop plants and unwanted plants. Preferably, the antidote is applied together with the herbicidal active ingredient. If the components are applied separately, the antidote is applied first to the field and then the herbicidal active ingredient. The herbicidal active ingredient and antidote may be formulated together or separately as spray agents in the form of suspensions, emulsions or solutions.

Treatment of the crop plant seed with the antidote prior to sowing is also feasible. The herbicidal active ingredient is then applied on its own in conventional manner.

For herbicidal (heteroaryloxy)-phenoxyacetic acid derivatives, the amount of antidotally active compound varies, depending on the crop. The ratios may vary over a wide range, and are also dependent on the structure of the (heteroaryloxy)phenoxyacetic acid derivatives and on the crop involved. Suitable ratios of herbicidal active ingredient to antidote are from 1:10 to 1:0.01, and preferably from 1:4 to 1:0.1, parts by weight.

For the same cyclohexenone derivative, the amount of antidote varies, depending on the crop. The ratios in which a cyclohexenone derivative and a 1,8-naphthyridine derivative I are used may vary over a wide range, and are dependent on the structure of the cyclohexenone derivative, the naphthyridine derivative I and the crop involved. Suitable ratios of herbicidal active ingredient to safener are from 1:10 to 1:0.01, and preferably from 1:4 to 1:0.25, parts by weight.

The novel herbicidal agents may contain, in addition to the naphthyridine derivative I as safener and the herbicide from the group of the (heteroaryloxy)phenoxyacetic acids IV or cyclohexenones V, other herbicidal or growth-regulating active ingredients of different chemical structure without the safening effect being impaired.

The agents according to the invention, or—when applied separately—the herbicidal active ingredients and the safener, are applied for instance in the form of directly sprayable solutions, powders, suspensions (including high-percentage aqueous, oily or others), dispersions, emulsions, oil dispersions, pastes, dusts, broadcasting agents or granules by spraying, atomizing, dusting, broadcasting or pouring. The forms of application depend entirely on the purpose for which the active ingredients are to be used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredients and/or antidotes as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the herbicidal active ingredients and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably from 0.5 to 90, wt % of herbicidal active ingredient and antidote. The herbicidal active ingredient is applied at rates of from 0.2 to 5 kg/ha.

The present invention is further illustrated by the following examples.

EXAMPLE 1

2-Amino-5-chloromethyl-7-hydroxy-1,8-naphthyridine 32.9 g (0.2 mol) of ethyl 4-chloroacetoacetate is dripped into a suspension of 21.8 g (0.2 mol) of 2,6-diaminopyridine in 100 ml of 85% strength phosphoric acid. The reaction mixture is stirred for 3 hours at 90° C., cooled and poured into ice water, followed by neutralization with concentrated aqueous ammonia solution. The precipitate is suction filtered, stirred into water again and finally boiled with acetonitrile. 22.8 g (54%) of the title compound is obtained; m.p.: >280° C.

EXAMPLE 2

2-Amino-5-methoxymethyl-7-hydroxy-1,8-naphthyridine

A mixture of 21.8 g (0.2 mol) of 2,6-diaminopyridine and 29.2 g (0.2 mol) of methyl 4-methoxyacetoacetate in 400 ml of glacial acetic acid is stirred under reflux for 3 hours. After cooling, the precipitate is suction filtered and stirred with 150 ml of cold ethanol. 8 g (20%) of the title compound is obtained; m.p.: >290° C.

EXAMPLE 3

Acetylation of 2-amino-5,7-dihydroxy-1,8-naphthyridine

A mixture of 17.7 g (0.1 mol) of 2-amino-5,7-dihydroxy-1,8-naphthyridine prepared in accordance with Lit.[3] and 250 ml of acetic anhydride is stirred under reflux for 30 minutes. After cooling, the precipitate is suction filtered, washed with acetone and dried. There is obtained 20.9 g (80%) of a mixture of 2-acetylamino-5-hydroxy-7-acetoxy-1,8-naphthyridine and 2-acetylamino-5-acetoxy-7-hydroxy-1,8-naphthyridine; m.p.: >300° C. This mixture can be used direct in the chlorination with POCl₃ described below.

EXAMPLE 4

2-Amino-5,7-dichloro-1,8-naphthyridine

A suspension of 63 g (0.241 mol) of the mixture prepared in Example 3 and 600 ml of POCl₃ is slowly heated to the reflux temperature and then stirred for 2 hours under reflux. Subsequently, the reaction mixture, which has been concentrated to about half its volume, is carefully dripped with ice cooling into 2.5 liters of ice water. The resulting mixture is stirred for one hour at 95°-100° C. and then cooled, the residue is filtered off and the filtrate is brought to a pH of 6. The precipitate is suction filtered, washed thoroughly with warm water and dried. There is obtained 47.9 g (92%) of the title compound; m.p.: 213°-216° C.

EXAMPLE 5

2-Amino-5-methyl-7-methylthio-1,8-naphthyridine 77.5 g (0.4 mol) of 2-amino-5-methyl-7-chloro-1,8-naphthyridine prepared in accordance with Lit.[5] is introduced into a solution of 112 g (1.6 mol) of sodium thiomethanolate in 700 ml of water, and the resulting suspension is refluxed for 4 hours. After cooling, the residue is suction filtered, washed with water and dried. There is obtained 68 g (83%) of the title compound; m.p.: 204°-209° C.

EXAMPLE 6

2-Hydroxysulfonyl-5,7-dimethyl-1,8-naphthyridine 9.6 g (50 mmol) of 2-chloro-5,7-dimethyl-1,8-naphthyridine prepared in accordance with Lit.[8),9)] is introduced into a solution of 8.2 g (65 mmol) of sodium sulfite in 40 ml of water which has been adjusted to a pH of 7-8 with dilute aqueous hydrochloric acid. The suspension which is obtained is heated for 12 hours under reflux. After cooling, solid residues are removed from the solution and the solution itself is acidified with aqueous hydrochloric acid (pH about 1). The acidified solution is left for 12 hours at 0° to 5° C., the product crystallizing out. There is obtained 7.7 g (65%) of the title compound; m.p.: >280° C.

The compounds listed in Table 1 below were prepared from corresponding starting materials after appropriate modification of the details of Examples 1 to 6.

TABLE 1

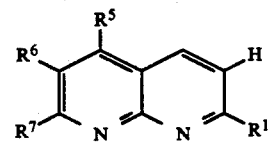

| Example No. | R¹ | R⁵ | R⁶ | R⁷ | mp (°C.) | Lit.[a)] |
|---|---|---|---|---|---|---|
| 1.1 | NHCOCH₃ | OH | H | H | 264-265 | 10) |
| 1.2 | NH₂ | Cl | H | Cl | 213-216 | |
| 1.3 | NH₂ | OH | H | H | >300 | 10) |
| 1.4 | NH₂ | CH₃ | H | H | >300 | 1) |
| 1.5 | HNCOCH₃ | phenyl | H | CH₃ | 207-213 | 5) |
| 1.6 | HNCOCH₃ | CH₃ | H | OC₆H₅ | 203-205 | |
| 1.7 | NH₂ | OH | CO₂H | H | >300 | 10) |
| 1.8 | NH₂ | H | H | Cl | >300 | |
| 1.9 | HNCOCH₃ | OH | CO₂C₂H₅ | H | >300 | 10) |
| 1.10 | NH₂ | CH₂Cl | H | Cl | >280 | |
| 1.11 | NH₂ | CH₂OCH₃ | H | OH | >290 | |

TABLE 1-continued

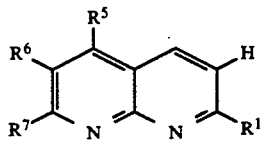

| Example No. | R¹ | R⁵ | R⁶ | R⁷ | mp (°C.) | Lit.[a] |
|---|---|---|---|---|---|---|
| 1.12 | HNCOCH₃ | H | H | OH | >280 | [11] |
| 1.13 | NH₂ | H | H | CH₃ | 238 (decomp) | [12] |
| 1.14 | NH₂ | H | H | OH | >280 | [2],[11] |
| 1.15 | NH₂ | C₆H₅ | H | CH₃ | 246 (decomp) | [4] |
| 1.16 | NH₂ | CH₃ | H | SCH₃ | 204–209 | |
| 1.17 | NH₂ | CH₃ | H | OC₆H₅ | 206–210 | [5] |
| 1.18 | NH₂ | CH₃ | H | C₆H₅ | >280 | [1],[4] |
| 1.19 | HNCOCH₃ | CH₂Cl | H | OH | >280 | |
| 1.20 | NH₂ | CH₂Cl | H | OH | >280 | |
| 1.21 | NH₂ | Br | H | Br | 208–212 | |
| 1.22 | NH₂ | CH₃ | H | Br | >300 | |
| 1.23 | NH₂ | CH₃ | H | N(CH₃)₂ | >300 | |
| 1.24 | NH₂ | H | CO₂C₂H₅ | OH | >300 | [11] |
| 1.25 | SH | CH₃ | H | CH₃ | 272–274 | |
| 1.26 | NH₂ | CF₃ | H | CF₃ | 204–208 | [13] |
| 1.27 | NH₂ | OH | H | OH | 325 (decomp) | [3] |
| 1.28 | SCH₂C₆H₅ | CH₃ | H | CH₃ | 98–104 | |
| 1.29 | NH₂ | CH₃ | H | OCH₃ | 229–232 | |
| 1.30 | NH₂ | CH₃ | H | Cl | 256–261 | [5] |
| 1.31 | HNCOCH₃ | CH₃ | H | Cl | 238–240 | [5] |
| 1.32 | OCH₃ | CH₃ | H | CH₃ | 37–40 | [9] |
| 1.33 | Cl | CH₃ | H | CH₃ | 138–141 | [8],[9] |
| 1.34 | HNCOCH₃ | CH₃ | H | OH | 395 | [5] |
| 1.35 | OH | CH₃ | H | CH₃ | 253–257 | [8],[9] |
| 1.36 | NH₂ | CH₃ | H | OH | >300 | [6] |
| 1.37 | NH₂ | CH₃ | H | CH₃ | 218–220 | [7] |
| 1.38 | NH₂ | CF₃ | H | CH₃ | 185–187 | [13] |
| 1.39 | NH₂ | CH₃ | H | CF₃ | 244–246 | [13] |
| 1.40 | NH₂ | OCH₃ | H | OCH₃ | 230–232 | [13] |
| 1.41 | SO₃H | CH₃ | H | CH₃ | >280 | |

[a] Literature sources
[1] R. A. Henry and P. R. Hammond, J. Het. Chem. 14, 1109 (1977)
[2] S. Carboni, A. Da Settimo and G. Pirisino, Ann. di Chim. 54, 883 (1964)
[3] G. R. Lappin, Q. R. Petersen and C. E. Wheeler, J. Org. Chem. 15, 377 (1950)
[4] A. Mangini and M. Colonna, Gazz. chim. ital. 73, 330 (1943)
[5] V. Petrow, E. L. Rewald and B. Sturgeon, J. Chem. Soc. London 1407 (1947)
[6] O. Seide, Chem. Ber. LIX, 159 (1926).
[7] J. Bernstein et al., J. Am. Chem. Soc. 69, 1157 (1947)
[8] A. Mangini and M. Colonna, Gazz. chim. ital. 73, 323 (1943)
[9] E. Ochiai and K. Miyaki, Chem. Ber. 74, 1115 (1941)
[10] S. Carboni, A. Da Settimo, P. L. Ferrarini and I. Tonetti, Gazz. chim. ital. 101, 129 (1972)
[11] S. Carboni, A. Da Settimo and P. L. Ferrarini, Gazz. chim. ital 95, 1492 (1965)
[12] E. V. Brown, J. Org. Chem. 30, 1607 (1965)
[13] E. Eichler, C. S. Rooney and H. W. R. Williams, J. Het. Chem. 13, 41 (1976)

EXAMPLE 7

2-Amino-6-bromo-5,7-dimethyl-1,8-naphthyridine 173 g (1 mol) of 2-amino-5,7-dimethyl-1,8-naphthyridine is suspended in 500 ml of glacial acetic acid. At 60° C. and with stirring, 160 g (1 mol) of bromine is dripped in, the solid going into solution. After all has been added, the mixture is stirred overnight at room temperature (20° C.) and then poured into 1 liter of water. Excess bromine is reduced by adding a small amount of NaHSO₃. The pH is brought to 4 with concentrated NH₃ solution. The mixture is stirred for about 30 minutes and the precipitate is filtered off and dried under reduced pressure to give 132 g of a pale brown solid.

EXAMPLE 8

2-Amino-5,6-dimethyl-7-phenylthio-1,8-naphthyridine 13 g of a 30% strength methanolic sodium methylate solution is introduced into 5.0 g (24 mmol) of 2-amino-7-chloro-5,6-dimethyl-1,8-naphthyridine and 8.0 g (72 mmol) of thiophenol in 100 ml of anhydrous methanol. The mixture is boiled under reflux for 3 hours and stirred overnight at room temperature. 200 ml of water is added, the mixture is stirred for 1 hour, and the precipitated solid is filtered off, washed with a small amount of methanol and dried under reduced pressure. There is obtained 4.7 g of a pale yellow solid.

EXAMPLE 9

2-Acetamino-7-hydroxy-5,6-dimethyl-1,8-naphthyridine 142 g (0.75 mol) of 2-amino-7-hydroxy-5,6-dimethyl-1,8-naphthyridine and 640 ml of acetic anhydride are boiled under reflux for 30 minutes. After the mixture has been cooled, the product is filtered off and purified by stirring with CH₂Cl₂ and methanol. There is obtained 64.1 g (37%) of a gray solid.

¹H-NMR (200 MHz, (F₃—(O₂D): δ=2.42 (s, 3H, CH₃), 2.58 (s, 3H, CH₃), 2.69 (s, 3H, CH₃), 7.46 (d, 1H, Ar—H), 8.84 (d, 1H, Ar—H).

EXAMPLE 10

2-Amino-7-chloro-5,6-dimethyl-1,8-naphthyridine 34.6 g (0.15 mol) of 2-acetamino-7-hydroxy-5,6-dimethyl-1,8-naphthyridine and 380 ml of phosphorus oxychloride are boiled under reflux for 30 minutes, the starting material dissolving. Excess POCl$_3$ is distilled off, the residue poured onto ice and concentrated hydrochloric acid is added. After the mixture has been boiled under reflux for 30 minutes, it is made alkaline with 50% strength sodium hydroxide solution. The precipitate is suction filtered and recrystallized from 4 liters of methanol. There is obtained 28.7 g (92%) of a pale brown solid which is further reacted without any purification.

The compounds listed in Table 2 below were prepared from corresponding starting materials with appropriate modification of the details of Examples 7, 8, 9 and 10.

TABLE 2

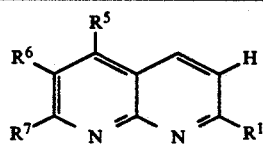

| Example No. | R$^1$ | R$^5$ | R$^6$ | R$^7$ | mp (°C.) | $^1$H-NMR (200 MHz, DMSO-D$_6$) δ [ppm] | Lit.[a)] |
|---|---|---|---|---|---|---|---|
| 2.1 | NH$_2$ | Cl | CH$_3$ | Cl | 150 (decomp) | 2.55(s, 3H, CH$_3$), 7.07(d, 1H Ar—H), 7.85(S(br.), 2H, NH$_2$), 8.23(d, 1H, Ar—H). | |
| 2.2 | NH$_2$ | Cl | i-C$_3$H$_7$ | Cl | >145 (decomp) | 1.42(d, 6H, CH$_3$), 3.90 (n, 1H, CH(CH$_3$)$_2$), 7.10(d, 1H, Ar—H), 8.10 (s(br.), 2H, NH$_2$), 8.30(d, 1H, Ar—H). | |
| 2.3 | NH$_2$ | Cl | n-C$_3$H$_9$ | Cl | 220–225 | 0.94(t, 3H, CH$_3$), 1.46(m, 4H, (CH$_2$)$_2$), 2.94(t, 2H, Ar—CH$_2$, 7.34(d, 1H, Ar—H), 8.46(d, 1H, Ar—H) 8.85(s.(br.), 2H, NH$_2$). | |
| 2.4 | NH$_2$ | OH | i-C$_3$H$_7$ | OH | >250 | 1.28(d, 6H, CH$_3$), 3.38(h, 1H, (CH$_3$)$_2$CH), 6.33(d, 1H, Ar—H), 7.30(s(brs.), 2H, NH$_2$), 7.94 (d, 1H, Ar—H), 9.95(s(br.), 1H, OH, 11.79(s, 1H, OH). | |
| 2.5 | NH$_2$ | OH | CH$_3$ | OH | >200 | | |
| 2.6 | NH$_2$ | CH$_3$ | CH$_3$ | CH$_3$ | >230 | 2.27(s, 3H, CH$_3$), 2.45 (s, 3H, CH$_3$), 2.52(s, 3H, CH$_3$), 6.49(s, 2H, NH$_2$), 6.23(d, 1H, Ar—H), 8.09(d, 1H, Ar—H). | 14),15) |
| 2.7 | NH$_2$ | CH$_3$ | Cl | CH$_3$ | | 2.55(s, 3H, CH$_3$), 2.60(s, 3H, CH$_3$), 5.90(s(Brs.), 2H, NH$_2$), 6.82(d, 1H, Ar—H), 8.13(d, 1H, Ar—H). | |
| 2.8 | NH$_2$ | CH$_3$ | Br | CH$_3$ | | 2.61(s, 3H, CH$_3$), 2.63(s, 3H, CH$_3$), 6.85(d, 1H, Ar—H), 7.2(s(brs.), 2H, NH$_2$), 8.10 (d, 1H, Ar—H). | |
| 2.9 | NH$_2$ | CH$_3$ | CH$_3$ | OH | >190 (decomp) | 2.5(s, 6H, CH$_3$), 4.5(s(brs.), 2H, NH$_2$), 6.0(d, 1H, Ar—H), 7.38 (d, 1H, Ar—H). | 16) |
| 2.10 | NH$_2$ | CH$_3$ | i-C$_3$H$_7$ | OH | | 1.50(d, 6H, CH$_3$), 2.77(s, 3H, Ar—CH$_3$), 7.17(d, 1H, Ar—H, 8.42(d, 1H, Ar—H). (in trifluoroacetic acid) | |
| 2.11 | NH$_2$ | CH$_3$ | CH$_3$ | Cl | brown oil | | |
| 2.12 | NH$_2$ | CH$_3$ | i-C$_2$H$_7$ | Cl | brown oil | | |
| 2.13 | NH$_2$ | CH$_3$ | CH$_3$ | OCH$_3$ | | 2.18(s, 3H, Ar—CH$_3$), 2.40(s, 3H, Ar—CH$_3$), 3.95(s, 3H, OCH$_3$), 6.60(s, 2H, NH$_2$), 6.63(d, 1H, Ar—H), 7.99(d, 1H, Ar—H). | |
| 2.14 | NH$_2$ | CH$_3$ | CH$_3$ | SC$_6$H$_5$ | | 2.32(s, 3H, CH$_3$), 2.44(s, 3H, CH$_3$), 6.65(s, 2H, NH$_2$), 6.70 (d, 1H, Ar—H), 7.45–7.6(m, 5H, s-Ph), 8.10(d, 1H, Ar—H). | |
| 2.15 | NHCOCH$_3$ | CH$_3$ | CH$_3$ | OH | | 2.42(s, 3H, CH$_3$), 2.58 (s, 3H, CH$_3$), 2.69(s, 3H, CH$_3$), 7.46 (d, 1H, Ar—H), 8.84(d, 1H, Ar—H) | |

TABLE 2-continued

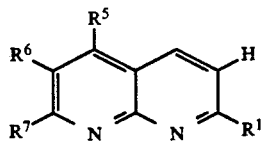

| Example No. | R¹ | R⁵ | R⁶ | R⁷ | mp (°C.) | ¹H-NMR (200 MHz, DMSO-D₆) δ [ppm] | Lit.[a] |
|---|---|---|---|---|---|---|---|
| 2.16 | (2,6-dichlorophenyl-NHCO-) | CH₃ | H | CH₃ | 287–291 | | |
| 2.17 | NHCOC₆H₅ | OH | CO₂CH₂CH₃ | H | 235–240 | | |

(decomp) = melts with decomposition
[a]Literature:
[14]US-A 4,133,885
[15]W. A. Bolhofer el al. J. Med. Chem. 22(3), 301 (1979)
[16]CA-A 1,088,659

EXAMPLES DEMONSTRATING BIOLOGICAL ACTION

The influence of various representatives of the herbicidal agents, or combinations of herbicide and antidote, according to the invention on the growth of unwanted and crop plants compared with the herbicidal active ingredient alone is illustrated in the following greenhouse experiments.

The vessels employed were plastic flowerpots having a volume of 300 cm³ and filled with a sandy loam containing about 3.0% humus. The seeds of the test plants were sown separately, according to species, and then moistened. The vessels were then covered with transparent plastic hoods until the plants had taken root.

For the postemergence treatment, the plants were grown, depending on growth form, to a height of 3 to 20 cm before being treated with the active ingredients, which were suspended or emulsified in water and sprayed through finely distributing nozzles.

As an example of a herbicidal active ingredient of the formula V, the cyclohexenone derivative V.2 was used in the biological experiments:

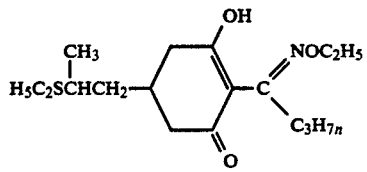

The herbicidal active ingredient V.2 was used (on its own and together with the safener) in the spray liquor as a commercially formulated product (184 g/l EC) together with the same amounts of solvent system XXII given in the table for the safener.

For the postemergence treatment, all the safeners were formulated in a mixture consisting of 80% of cyclohexenone and 20% of Emulphor EL (formulation XXII) with 10 wt % of active ingredient.

The test plants employed were *Hordeum vulgare, Lolium multiflorum, Oryza sativa, Setaria italica,* Sorghum, *Triticum aestivum* and *Zea mays.*

The vessels were set up in the greenhouse, heat-loving species at from 18° to 30° C. and species from more moderate climates at from 10° to 25° C.

The experiments were run for from 3 to 5 weeks. During this period, the plants were tended and their reactions to the various treatments assessed.

Damage by the chemical agents was assessed on a scale from 0 to 100% compared with the untreated control plants, 0 denoting no damage and 100 denoting complete destruction of the plants.

The tables below document the safening action of compounds nos. 1.10, 1.16, 1.8, 1.17 and 2.13 according to the invention. These compounds significantly improve the tolerance of the herbicide V.2 by wheat.

TABLE 1

Improvement in the tolerance of the herbicide V.2 by wheat by admixing a safening compound and applying the mixture postemergence in the greenhouse

| Appl. rate kg/ha | | Test plants and % damage | |
|---|---|---|---|
| | | Crop plant | Unwanted plant |
| Herbicide V.2 | Safener 1.10 | *Triticum aestivum** | *Lolium multif.* |
| 0.03 | — | 65 | 100 |
| 0.06 | — | 95 | 100 |
| 0.03 | 0.125 | 0 | 100 |
| 0.06 | 0.25 | 30 | 100 |

*Variety: "Okapi"

TABLE 2

Reduction in the phytotoxicity of the herbicide V.2 in wheat by combining it with an example of a safener and applying the mixture postemergence in the greenhouse

| Appl. rate kg/ha | | Test plants and % damage | |
|---|---|---|---|
| | | Crop plant | Unwanted plant |
| Herbicide V.2 | Safener 1.16 | *Triticum aestivum** | *Lolium multif.* |
| 0.03 | — | 65 | 100 |
| 0.03 | 0.125 | 0 | 100 |

*Variety: "Okapi"

TABLE 3

Reduction in the phytotoxicity of the herbicide V.2 in wheat by combining it with an example of a safener and applying the mixture postemergence in the greenhouse

| Appl. rate kg/ha | | Test plants and % damage | |
| --- | --- | --- | --- |
| Herbicide V.2 | Safener [No.] | Crop plant *Triticum aestivum*\* | Unwanted plant *Lolium multif.* |
| 0.03 | — | 65 | 100 |
| 0.03 | 0.125 [1.8] | 30 | 100 |
| 0.03 | 0.125 [1.17] | 20 | 100 |

\*Variety: "Okapi"

TABLE 4

Reduction in the phytotoxicity of the herbicide V.2 in rice by combining it with an example of a safener and applying the mixture postemergence in the greenhouse

| Appl. rate [kg/ha] | | Test plants and % damage | |
| --- | --- | --- | --- |
| Herbicide | Safener 2.13 | Crop plant *Oryza sativa*\* | Unwanted plant *Setaria italica* |
| 0.03 | — | 50 | 95 |
| 0.03 | 0.06 | 10 | 80 |

\*Variety: "Bahia"

We claim:

1. A herbicidal composition containing a safening effective amount of at least one substituted 1,8-naphthyridine of the formula I $$\underset{R^7}{\overset{R^5}{\underset{N}{\bigvee}}}\overset{R^6}{\underset{N}{\bigvee}}R^1 \qquad I$$

where
R$^1$ is amino or NHR$^2$ where R$^2$ is a group $$-\overset{O}{\underset{\|}{C}}-A$$

where
A is C$_1$-C$_8$-alkyl,
R$^5$ and R$^7$ are each hydrogen, C$_1$-C$_{12}$-alkyl, C$_1$-C$_4$-alkoxy or C$_1$-C$_4$-alkylthio, and
R$^6$ is hydrogen, C$_1$-C$_4$-alkoxycarbonyl, or a plant-tolerated salt thereof, and a herbicidally effective amount of
b) a cyclohexenone derivative of the formula V $$V$$

where
R$^d$ is C$_1$-C$_4$-alkyl
R$^e$ is C$_1$-C$_4$-alkyl, C$_3$-C$_4$-alkenyl, C$_3$-C$_4$-haloalkenyl or thenyl which may be substituted by a halogen atom;
R$^f$ is C$_1$-C$_4$-alkyl which may be mono- or disubstituted by C$_1$-C$_4$-alkylthio;
R$^g$ is hydrogen;
R$^h$ is hydrogen and
R$^i$ is hydrogen.

2. A herbicidal composition as defined in claim 1, wherein in the substituted 1,8-naphthyridine of the formula I, R$^1$ is amino.

3. A herbicidal composition as defined in claim 1, wherein the weight ratio of the components of the formula I and of the formula V is from 10:1 to 0.01:1.

4. A process for the selective control of unwanted plants in crops, wherein a safening effective amount of a substituted 1,8-naphthyridine of the formula I as set forth in claim 1 and a herbicidally effective amount of a cyclohexenone derivative of the formula V as set forth in claim 1 are applied either simultaneously or one after the other in any order before, during or after sowing of the crop plants or before or during emergence of the crop plants.

5. A process for preventing damage to crop plants by herbicidal cyclohexenone derivatives of the formula V as set forth in claim 1, wherein the seed of the crop plants is treated with a safening effective amount of a substituted 1,8-naphthyridine of the formula I as set forth in claim 1.

6. A process for the selective control of unwanted plants in crops, wherein the leaves of the crop plants and the unwanted plants are treated post-emergence and either simultaneously or one after the other with a safening effective amount of a substituted 1,8-naphthyridine of the formula I as set forth in claim 1 and with a herbicidally effective amount of a cyclohexenone derivative of the formula V as set forth in claim 1.

7. A process as set forth in claim 4, wherein the crop plants are barley, wheat, Indian corn, sorghum or rice.

8. A process as set forth in claim 5, wherein the crop plants are barley, wheat, Indian corn, sorghum or rice.

9. A process as set forth in claim 6, wherein the crop plants are barley, wheat, Indian corn, sorghum or rice.

* * * * *